United States Patent [19]

Chwang

[11] Patent Number: 4,652,554
[45] Date of Patent: Mar. 24, 1987

[54] NITRO-SUBSTITUTED 1-β-D-ARABINOFURANOSYLCYTOSINES

[75] Inventor: Tek L. Chwang, Memphis, Tenn.

[73] Assignee: St. Jude Children's Research Hospital, Memphis, Tenn.

[21] Appl. No.: 350,778

[22] Filed: Feb. 22, 1982

[51] Int. Cl.[4] ...................... C07H 17/00; A61K 31/70
[52] U.S. Cl. .......................................... 514/49; 536/23
[58] Field of Search ............................. 536/23; 514/49

[56] References Cited

U.S. PATENT DOCUMENTS 3,595,853  7/1971  Kanai et al. ............................ 536/23

OTHER PUBLICATIONS

Goodman and Gilman, *The Pharmacological Basis of Therapeutics* (3rd Ed., 1966), pp. 1345–1379.
Goodman and Gilman, ibid, (6th Ed., 1980), pp. 1256–1301.
*Therapaeia*, May 1981, pp. 11–27.
Cancer Facts and Figures *Am. Can. Soc.* (1970), pp. 3–5, 16–19.
Ibid (1983), p. 3–7, 12–19.
Furth and Cohen, *Can. Res.*, 28, 2061 (1968).
Chwang, Fridland and Avery, *J. Med. Chem.*, 28, 280 (1983).
Ho, *Cancer Research*, 33, 2816 (1973).
Matsushita et al., *Cancer Research*, 41, 2707 (1981).
Gray et al., *Biochemical Pharmacology*, 21, 465 (1972).
Kataoka and Sakurai, "Research Results in Cancer Research", 70, 147–151 (Editors, Carter & Sakurai, Springer-Verlag, New York 1980).
Bobek et al., *J. Med. Chem.*, 21, 597 (1978).
Cheng et al., *Cancer Research*, 41, 3144 (1981).
Kreis et al., *Helv. Chim. Acta.*, 61, 1011 (1978).
Venditti et al., *Can. Chem. Rep.*, 56, 483 (1972).
Burgess et al., *Can. Treat. Rep.*, 61, 437 (1977).
Hamamura et al., *J. Med. Chem.*, 663 (1966).
Kondo et al., *J. Org. Chem.*, 45, 1577 (1980).
Chwang et al., AACR Abstracts, Mar. 1981, Abstract 895.

Primary Examiner—Alan Siegel
Attorney, Agent, or Firm—Leroy Whitaker; James L. Rowe

[57] ABSTRACT

1-(2-O-Nitro-β-D-arabinofuranosyl)cytosine and salts, anti-leukemics.

5 Claims, No Drawings

NITRO-SUBSTITUTED 1-β-D-ARABINOFURANOSYLCYTOSINES

BACKGROUND OF THE INVENTION

The nucleic acids, ribonucleic acid (RNA) and deoxyribonucleic acid (DNA), consist of long chains of alternating sugar and phosphate residues to each of which sugars is attached a nitrogenous base. The nitrogenous base is either a substituted purine or a substituted pyrimidine. Purine bases found in DNA and RNA include adenine, guanine, hypoxanthine, 1-methylhypoxanthine, 1-methylguanine and $N^2$-dimethylguanine. Pyrimidine bases found in nucleic acids include cytosine, thymine, uracil and 5-methylcytosine. The 5-carbon sugar derivatives of a purine or pyrimidine base are called nucleosides. For example, the nucleosides derived from cytosine include cytidine (cytosine plus ribose) and deoxycytidine (cytosine plus deoxyribose). A nucleoside with a phosphate group attached is called a nucleotide, for example, cytidine-3'-monophosphate (also known as 3'-cytidylic acid).

Both RNA and DNA are involved in the replication of viruses and in the growth of neoplasms. One of the more fruitful approaches to the therapy of viral disease or of neoplastic disease includes the use of drugs which are metabolic competitors (anti-metabolites) of naturally occurring nucleosides, nucleotides or nucleic acids. 5-Fluorouracil and 8-azaguanine are examples of such anti-metabolites. It is also possible to prepare anti-metabolites of the sugar portion of a nucleoside, as for example, the drug cytarabine which which is 1-β-D-arabinofuranosylcytosine in which arabinose is substituted for the ribose of cytidine. Cytosine itself is 4-amino-2-oxo-1,2-dihydropyrimidine. In the naturally occurring nucleosides, cytosine would be attached through $N^1$ to D-ribofuranoside, rather than D-arabinofuranoside as in cytarabine. Cytarabine (also known as cytosinearabinoside, arabinosylcytosine or ara-C) has been found to be active in several experimental tumors in animals and is presently used clinically for the treatment of acute leukemia. Resistance to the action of cytarabine occurs where the tumor or the surrounding tissue has high concentrations of cytidine deaminase, an enzyme which converts cytarabine to arabinosyluracil, an inactive compound.

It is an object of this invention to prepare a derivative of arabinofuranosylcytosine which is resistant to the action of cytidine deaminase.

DESCRIPTION OF THE INVENTION

In fulfillment of the above and other objects, this invention provides 1-(2-O-nitro-β-D-arabinofuranosyl)-cytosine, also referred to as nitrara-C, represented by the formula:

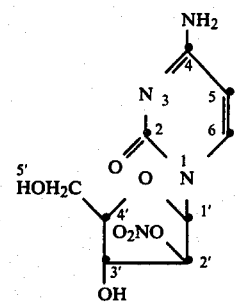

and pharmaceutically-acceptable acid addition salts thereof.

4-Amino-1-(2-O-nitro-β-D-arabinofuranosyl)-2-(1H)-pyrimidinone is an alternate systematic name for nitrara-C.

Although nitrara-C (I above) contains 3 nitrogen atoms, only the amino group at C-4 is sufficiently basic to form acid addition salts under ordinary conditions.

The pharmaceutically-acceptable acid addition salts of nitrara-C include salts derived from inorganic acids such as: hydrochloric acid, nitric acid, phosphoric acid, sulfuric acid, hydrobromic acid, hydriodic acid, phosphorous acid and the like, as well as salts derived from organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

1-(2-O-Nitro-β-D-arabinofuranosyl)cytosine is prepared according to the following reaction scheme:

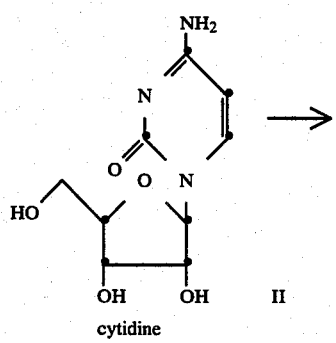

cytidine

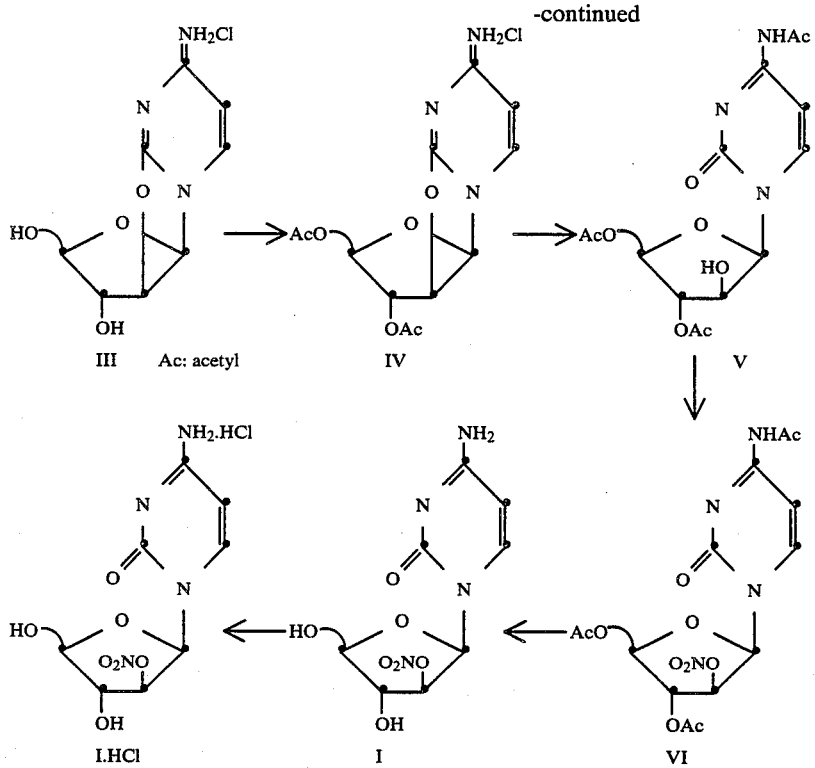

According to the Reaction Scheme, cytidine (II) is transformed to O², 2'-cyclocytidine (III) by the procedure of Kanai et al., *Chem. Pharm. Bull.*, 18, 2569 (1970). See also Walwick et al., *Proc. Chem. Soc.*, 84 (1959); Doerr et al., *J. Org. Chem.*, 32, 1462 (1967); and Ruyle et al., *J. Med. Chem.*, 10, 331 (1967). This compound is then diacetylated following the procedure of Hamamura et al., ibid, 19, 663 (1976). Addition of acetic anhydride and triethylamine to the diacetoxy intermediate gives 1-(3,5-di-O-acetyl-β-D-arabinofuranosyl)-N⁴-acetylcytosine. Nitration of this compound with fuming nitric acid in acetic anhydride yields the corresponding 1-(2-O-nitro-3,5-di-O-acetyl-β-D-arabinofuranosyl)-N⁴-acetylcytosine (VI). The acetyl groups are removed therefrom by treatment with barium methoxide in anhydrous methanol, thus yielding 1-(2-O-nitro-β-D-arabinofuranosyl)cytosine (I), the compound of this invention. This free base can readily be transformed to a salt form with a pharmaceutically acceptable acid such as hydrochloric acid to give the corresponding hydrochloride salt (I.HCl).

The above synthetic procedure is illustrated in part by the following example.

EXAMPLE 1

A. Preparation of 2,2'-Anhydro-1-(3,5-di-O-acetyl-β-D-arabinofuranosyl)cytosine hydrochloride (IV)

Following the general procedure of Hamamura et al., *J. Med. Chem.*, 19, 663 (1976), to a stirred suspension of 2,2'-anhydro-1-β-D-arabinofuranosylcytosine hydrochloride (III) [furnished by the procedure of Kenai et al., *Chem. Pharm. Bull.*, 18, 2569 (1970)] (10.47 g. 40 mmol) in N,N-dimethylacetamide (200 ml.) was added acetyl chloride (13.25 g. 169 mmol). The reaction mixture, protected from moisture with a drying tube packed with Drierite, was stirred at 37° C. for 24 hours. The cooled mixture was then added to diethyl ether (1000 ml.). The resulting mixture was allowed to stand at ambient temperature for 3 hours, during which time a solid precipitated. The collected precipitate was washed with diethyl ether, and crystallized from acetonitrile; 12.31 g. (89%) of pure 2,2'-anhydro-1-(3,5-di-O-acetyl-β-D-arabinofuranosyl)cytosine hydrochloride, m.p. 217.6–218.8° C. with decomposition, were obtained. The UV absorption maxima for IV agreed well with those previously reported: (0.1N HCl) 262 and 232 nm (ε 11030 and 9330), (0.1N NaOH) 273 nm (ε 10820), (96% ethanol) 263 and 235 nm (ε 10680 and 9360).

The compound had the following further physical properties: $^1$H NMR (DMSO-$d_6$+$D_2O$) δ1.85 (s, 3, OAc), 2.10 (s, 3, OAc), 4.10–4.30 (m, 2, H-5'), 4.60–4.71 (m, 1, H-4'), 5.34–5.39 (m, 1, H-3'), 5.76 (d, J=6 Hz, 1, H-2'), 6.65 (d, J=6 Hz, 1, H-1'), 6.83 (d, JW =7.6 Hz, 1, H-5), 8.38 (d, J=7.6 Hz, 1, H-6); IR (KBr) 3275, 3010, 2965, 1765, 1745, 1675, 1650, 1540, 1490, 1370, 1265, 1235, 1220, 1210, 1100 cm$^{-1}$;

$[\alpha]_D^{33}$ −64±0.4° (c 1.00, methanol).

B. 1-(3,5-Di-O-acetyl-β-D-arabinofuranosyl)-N⁴-acetylcytosine (V)

To a stirred suspension of 2,2'-anhydro-1-(3,5-di-O-acetyl-β-D-arabinofuranosyl)cytosine hydrochloride (7.60 g., 22 mmol) in tetrahydrofuran (THF) (400 ml) were added acetic anhydride (3.33 g., 33 mmol) and triethylamine (2.56 g., 25 mmol). The reaction mixture was stirred at room temperature for 7 days during which time 1-(2,5-di-O-acetyl-β-D-arabinofuranosyl)-N⁴-acetylcytosine precipitated. The precipitate was collected by filtration and the filter cake washed with THF (2×50 ml), ice water (2×100 ml) and finally with THF (50 ml) again to give 4.45 g. (55%) of 1-(3,5-di-O-acetyl-β-D-arabinofuranosyl)-N⁴-acetylcytosine. Another 895 mg. (11%) of product were recovered from the THF mother liquors. The pooled crude product was recrystallized from 96% ethanol and the precipitate collected by centrifugation to yield 4.33 g. (53%) of pure 1-(3,5-di-O-acetyl-β-D-arabinofuranosyl)-N[4]-acetylcytosine, m.p. 233°–234.1° C. dec.

The compound had the following physical properties: UV absorption maxima (0.1N HCl) 307 and 240 nm (ε 13610 and 9100), (0.1N NaOH) 303 and 276 nm (ε 9270 and 9240), (96% ethanol) 299 and 247 nm (ε8000 and 15490).

$^1$H NMR (DMSO-$d_6$+$D_2O$) δ 2.01 (s, 3, NAc), 2.07 (s, 6, OAc), 4.14–4.26 (m, 4, H-2', H-4'and H-5'), 4.84–4.86 (m, 1, H-3'), 5.95 (d, J=3.4 Hz, 1, H-1'), 7.08 (d, J=7.5 Hz, 1, H-5), 7.80 (d, J=7.5 Hz, 1, H-6).

IR spectrum: (KBr) ν at 3310, 1740, 1720, 1660, 1615, 1565, 1495, 1440, 1390, 1320, 1310, 1250, 1130, 1110, 1090, 1040 cm$^{-1}$;

Rotation: $[\alpha]_D^{23}$ = +88.7°±0.7° (c 0.20, methanol).

Analysis: Calculated for $C_{15}H_{19}N_3O_8$ (mol wt, 369.34): C, 48.78; H, 5.19; N, 11.38. Found: C, 48.49; H, 5.37; N, 11.47.

C.
1-(2-O-Nitro-3,5-di-O-acetyl-β-D-arabinofuranosyl)-N[4]-acetylcytosine (VI)

Acetic anhydride (20 ml., 212 mmol) was added gradually to fuming nitric acid (20 ml., 477 mmol) with efficient stirring, while the temperature was kept between −30° to −35° C. by external cooling. While the mixture was being stirred vigorously, 1-(3,5-di-O-acetyl-β-D-arabinofuranosyl)-N[4]-acetylcytosine (10 g., 27 mmol) was added in batches to the homogeneous mixture while maintaining the temperature at about −30° C. The clear reaction mixture was allowed to warm gradually to 0° C. After being stirred for 30 minutes at this temperature, the solution was poured into a mixture of ice and saturated aqueous $(NH_4)_2SO_4$ solution (250 ml.) that was stirred until all the ice had melted. The aqueous phase was then extracted with ethyl acetate (3×250 ml). The combined extracts were washed with saturated aqueous sodium bicarbonate (2×200 ml.) and water (3×200 ml.), and was then dried ($Na_2SO_4$) Crude 1-(2-O-nitro-3,5-di-O-acetyl-β-D-arabinofuranosyl)-N[4]-acetylcytosine (10.66 g., 95%) was obtained by removing the ethyl acetate under reduced pressure. The solid residue was crystallized from ethyl acetate to obtain pure 1-(2-O-nitro-3,5-di-O-acetyl-β-D-arabinofuranosyl)-N[4]-acetylcytosine (9.65 g., 86% yield): m.p. 159.7°–160.6° C.

The compound had the following further physical properties: UV $\epsilon_{max}$ (0.1N HCl) 300 and 246 nm (ε 9790 and 12190), (96% ethanol) 297 and 249 nm (ε 6470 and 15000);

$^1$H NMR (DMSO-$d_6$+$D_2O$) δ 2.10 (s, 3, NAc), 2.40 (s, 6, OAc), 4.27–4.30 (m, 3, H-4' and H-5'), 5.32–5.42 (m, 1, H-3'), 5.83–5.93 (m, 1, H-2'), 6.31 (d, J=5 Hz, 1, H-1'), 7.62 (d, J=7.3 Hz, 1, H-5), 7.90 (d, J=7.3 Hz, 1, H-6);

IR spectrum: (KBr) ν at 3260, 1752, 1720, 1670, 1625, 1560, 1490, 1445, 1390, 1370, 1350, 1320, 1245, 1110, 1060, 900, 850 cm$^{-1}$;

Rotation: $[\alpha]_D^{23}$ = +94.2±0.6° (c 1.00, methanol).

Analysis: Calculated for $C_{15}H_{18}N_4O_{10}$ (mol wt, 414.33): C, 43.49; H, 4.38; N, 13.52. Found: C, 43.28; H, 4.52; N, 13.36.

D. 1-(2-O-Nitro-β-D-arabinofuranosyl)cytosine (I)

To a solution of 1-(2-O-nitro-3,5-di-O-acetyl-β-D-arabinofuranosyl)-N[4]-acetylcytosine (10 g., 24 mmol) in anhydrous methanol (425 ml) under an atmosphere of dry nitrogen was added 1.9N barium methoxide (5 ml., 9.5 meq) in methanol. The reaction mixture was stirred at room temperature under an inert atmosphere for one hour and was then neutralized with a cation exchange resin (90 g., Bio-Rex 70/H$^+$, 100–200 mesh )in the presence of water (5 ml). The resin was separated by filtration and washed with methanol. The combined filtrate and washings were evaporated under reduced pressure to yield crude 1-(2-O-nitro-β-D-arabinofuranosyl)cytosine (6.60 g., 95%), which was crystallized from $H_2O$ to yield pure 1-(2-O-nitro-β-D-arabinofuranosyl)cytosine (5.97 g., 86%): m.p. 151.3°–152.7° C.;

The compound had the following physical properties: UV spectrum: $\lambda_{max}$ (0.1N HCl) 275 nm (ε 12970), (0.1N NaOH) 268 and 230 nm (ε 9430 and 8380), (96% ethanol) 269 and 239 nm (ε 8400 and 7950), ($H_2O$) 268 and 231 nm (ε 8597 and 8243);

$^1$HMR (DMSO-$d_6$+$D_2O$) δ 3.60–3.80 (m, 3, H-4' and H-5'), 4.15–4.22 (m, 1, H-3'), 5.60 (t, J=5.3 Hz, 1, H-2'), 5.77 (d, J=7.6 Hz, 1, H-5), 6.28 (d, J=5.6 Hz, 1, H-1'), 7.68 (d, J=7.6Hz, 1, H-6);

IR spectrum: (KBr) ν at 3420, 3280, 3180, 2930, 1650, 1620, 1525, 1495, 1410, 1360, 1285, 1190, 1080, 1060, 1040, 1020, 835 cm$^{-1}$;

Rotation: $[\alpha]_D^{23}$ = +116.4±0.5° (c 1.00, $H_2O$).

Analysis: Calculated for $C_9H_{12}N_4O_7$ (mol wt, 288.23): C, 37.51; H, 4.20; N, 19.44. Found: C, 37.52; H, 4.01; N, 19.42.

The following example illustrates the preparation of salts.

EXAMPLE 2

Preparation of 1-(2-O-Nitro-β-D-arabinofuranosyl)cytosine hydrochloride (I.HCl)

A solution of 1-(2-O-nitro-β-D-arabinofuranosyl)cytosine [6.6 g., 23 mmol. which was a white foam that was homogeneous by TLC (upper phase of 4:2:1=ethyl acetate:$H_2O$:1-propanol)] in methanol was acidified with concentrated hydrochloric acid until the pH of the solution was ~1.0. A white solid began to separate immediately. The solvent was removed under reduced pressure, and the resulting residue was coevaporated with methanol (3×200 ml). The product thus obtained was dried in vacuo and crystallized from a mixture of 1:1=absolute ethanol: 96% ethanol. The crystals were collected by centrifugation to obtain pure 1-(2-O-nitro-β-D-arabinofuranosyl)cytosine hydrochloride (4.83 g., 65%): m.p.>170° C. dec. The salt had these physical characteristics:

UV $\lambda_{max}$ (0.1N HCl) 276 nm (ε 13280), (0.1N NaOH) 270 nm (ε 9290), (96% ethanol) 273 nm (ε 8730), ($H_2O$) 270 and 236 nm (ε 9446 and 7305);

$^1$H NMR (DMSO-$d_6$+$D_2O$) δ 3.48–3.54 (m, 3, H-4' and H-5'), 3.62–3.80 (m, 1, H-3', partially obscured by HDO resonances), 5.44 (t, J=5.2 Hz, 1, H-2'), 5.89–5.98 (two superimposing d, J=7.6 and 5.6 Hz, 2, H-5 and H-1'), 7.82 (d, J=7.6 Hz, 1, H-6);

IR spectrum: (KBr) ν at 3480, 3250, 3070, 2900, 2750, 2650, 1715, 1680, 1655, 1540, 1460, 1400, 1370, 1285, 1265, 1205, 1140, 1090, 1040, 1020, 870, 820 cm$^{-1}$;

Rotation: $[\alpha]_D^{23}$ = +84.9±0.5° (c 1.00, $H_2O$).

Analysis: Calculated for $C_9H_{13}ClN_4O_7$ (mol wt, 324.68): C, 33.29; H, 4.04; Cl, 10.92; N, 17.26. Found: C, 33.43; H, 4.11; Cl, 10.86; N, 16.98.

1-(2-O-Nitro-$\beta$-D-arabinofuranosyl)cytosine (nitrara-C) is a powerful anti-neoplastic agent particularly against the leukemias. The activity of the compound in vivo against L1210 leukemia transplanted into mice is demonstrated in the following experimental study.

B6D2F$_1$/J female mice weighing ~20 g. were inoculated intraperitoneally with $1 \times 10^5$ cells of the murine leukemia, L1210. Five days later, the leukemia cells were washed from the peritoneal cavities of untreated mice, and baseline counts were made. Concomitantly, other groups of mice were treated i.p. with either ara-C.HCl or nitrara-C.HCl. Each drug was administered at a level of 720 mg/kg in a volume of 0.01 ml/gm of mouse weight. Twenty-four hours later, on day 6, cells were washed from the peritoneal cavities of both treated and NaCl-injected mice, and cell numbers were compared.

Five days after the intraperitoneal inoculation of B6D2F$_1$/J mice with one hundred thousand cells of leukemia L1210, an average of 255 million cells were recovered from the abdominal compartments of untreated mice. Twenty-four hours later, this value had increased by 52 percent for NaCl-injected mice, but had declined by 90 percent for animals that received 720 mg/kg of nitrara-C and 77% for ara-C treated group.

In a similar further study, B6D2F$_1$/J female mice were inoculated i.p. with $3 \times 10^6$ cells of L1210. Treatment was started 24 hours after tumor implantation. Nitrara-C hydrochloride treatment regimens were as follows:

1. daily for 7 days
2. day 1 only
3. days 1 and 4 only
4. days 1, 4 and 7.

Injections of 0.9 percent saline were used as a control. The following results were obtained.

On regimen 1, statistically significant increase in life-span was obtained with dosages higher than 34 mg/kg. The 208 mg/kg dosage produced a 162% extension of life-span and higher dosage regimens produced indefinite cures (60 day survivors): 259 mg/kg, 3 survivors; 346 mg/kg, 1 survivor; 432 mg/kg, 2 survivors; 720 mg/kg, 1 survivor (5 mice per group).

A 2000 mg/kg dose extended lifespan by 57% on regimen 2, 120% with regimen 3 and 197 percent with regimen 4.

Toxic deaths were not seen on any of the above regimens at the highest dosages.

Experiments were also carried out to determine the growth potential of cultured human lymphoblasts in the presence of nitrara-C in tissue culture. These experiments were carried out as follows:

All human lymphoblast lines were grown as suspension cultures in spinner flasks at 37° C. in an atmosphere of 95% air and 5% $CO_2$ in a humidified chamber. The growth medium for CCRF-CEM (T-cells) was MEM/-Spinner Modified medium supplemented with 10% heat inactivated newborn calf serum. A subline of CCRF-CEM cells were selected for resistance to ara-C by growth in the continuous presence of sublethal concentrations of the drug. Both MOLT-4 (T-cells) and RMPI-6410 (B-cells) were grown in RPMI Medium 1640 medium also supplemented with 10% heat-inactivated newborn calf serum. The cells were grown at a density between 5 to $10 \times 10^4$/ml and 1 to $1.5 \times 10^6$/ml, and were subcultured every 3 or 4 days to maintain the culture in exponential growth.

Experiments to determine the growth potential of the above cultured human lymphoblastoid cells in various concentrations of ara-C and nitrara-C were done in tissue culture flasks. Small volumes of drugs were added to complete growth medium in triplicate flasks. After 48 hours, the number of control cells had typically doubled twice. The initial cell densities were subtracted from the final cell densities, and the number of cells in flasks containing the drugs were determined by Coulter counting and expressed as the percentage of the number of cells in the control.

Table 1 which follows gives the results of these experiments which was carried out as follows:

TABLE 1

CYTOTOXICITY OF NITRARA-C AND ARA-C AGAINST VARIOUS HUMAN LYMPHOBLASTOID CELL LINES

| Cell Line | $IC_{50}$ (molar conc. for 50% inhib. of cell growth) | |
|---|---|---|
| | Nitrara-C | Ara-C |
| CCRF-CEM (T-cells) | $6 \times 10^{-7}$ | $2 \times 10^{-8}$ |
| MOLT-4 (T-cells) | $4 \times 10^{-7}$ | $10^{-8}$ |
| RPMI-6410 (B-cells) | $6 \times 10^{-6}$ | $6 \times 10^{-8}$ |
| CCFR-CEM/ara-C (mutant)[a] | $10^{-3}$ | $10^{-4}$ |

[a]Deficient in deoxycytidine kinase.

The above study shows that nitrara-C is highly cytotoxic to various human leukemia cells in culture and that the activity compares favorably to that of ara-C. Furthermore, similar to ara-C, nitrara-C's cytotoxicity depends on phosphorylation.

It is an advantage of nitrara-C that it is not deaminated by cytidine deaminase, and thereby rendered ineffective as is ara-C. The determination of the effect of cytidine deaminase was carried out on these two substrates plus cytidine and 2'-deoxycytidine.

Cytidine deaminase was isolated and partially purified from mouse kidney acetone powder, according to the procedure reported by McCormack et al., *Biochem. Pharmacol.*, 29, 830 (1980). Thus, mouse kidney acetone powder (3 g. obtained from Sigma Chemical Co., St. Louis, Mo.) was extracted at 55°–60° C. for 5 minutes with phosphate buffer (pH 8.0, 0.05M). The extract was filtered through four layers of guaze bandage, and the remaining colloidal materials were removed by centrifugation at 20,000 g. for 10 minutes. The supernatant was then filtered through a Nalgene filter unit (0.45 μm grid membrane) to give a clear yellowish filtrate that was adjusted to 40% saturation by the addition of solid ammonium sulfate (24 g/100 ml. of filtrate) with stirring at room temperature, and stirring was continued for 30 minutes. After removal of the precipitate by centrifugation (20,000 g. for 30 minutes), the active supernatant was adjusted to 70% saturation by further addition of ammonium sulfate (24 g/100 ml of supernatant). The resulting precipitate, recovered by centrifugation (20,000 g. for 30 minutes), was dissolved in 4 ml. of phosphate buffer (pH 7.0, 0.05M) and dialyzed twice against 2 liters of the same buffer. The $K_m$ for deamination of cytidine with this preparation was found to be $6.7 \times 10^{-5}M$.

Protein content was determined by Bio-Rad Protein Assay. Cytidine deaminase activity was assayed spectrophotometrically at 37° C. by following the disappearance of absorbance at 290 nm that characterizes the conversion of cytidine to uridine. All reaction mixtures contained $2.5 \times 10^{-4}$M of substrate and 1.3 mg of enzyme protein in a final volume of 1.0 ml. of phosphate buffer (pH 7.0, 0.05M).

Table 2 below gives the substrate specificity for cytidine deaminase thus determined for cytidine, 2'-deoxycytidine, ara-C and nitrara-C.

TABLE 2

SUBSTRATE SPECIFICITY OF CYTIDINE DEAMINASE

| COMPOUND | RELATIVE INITIAL RATE |
|---|---|
| Cytidine | 100 |
| 2'-Deoxycytidine | 39 |
| Ara-C | 15 |
| Nitrara-C | <1 |

Ara-C and nitrara-C were treated with cytidine deaminase and the IC$_{50}$ for CCRF-CEM cells in tissue culture determined. Table 3 gives the results of this experiment.

TABLE 3

EFFECT OF CYTIDINE DEAMINASE ON THE CYTOTOXICITY OF ARA-C AND NITRARA-C FOR CCRF-CEM CELLS

| Drug | IC$_{50}$ (molar conc. for 50% inhib. of cell growth) | | |
|---|---|---|---|
| | Without Cytidine Deaminase | With Cytidine Deaminase | Drug Deactivated By Cytidine Deaminase |
| Ara-C | $3 \times 10^{-8}$ | $3 \times 10^{-7}$ | 90% |
| Nitrara-C | $6 \times 10^{-7}$ | $6 \times 10^{-7}$ | <1% |

It is apparent from the above that nitrara-C is potentially useful in treating tumors in hosts that are rich in cytidine deaminase where ara-C is ineffective. Furthermore, nitrara-C may be orally active since it will not be deaminated in the gut.

Nitrara-C, usually in the form of its hydrochloride salt, can be administered to humans suffering from leukemia as for example acute granulocytic leukemia in adults either orally or parenterally. For parenteral administration, the dosage is administered iv. The dosage rate is 5–500 mg. per square meter of body surface per day, the dose level depending on whether the drug is given rapidly or continuously. Drug administration is continued for from 5–7 days or until severe leukopenia develops. The drug is supplied as a lyophilized powder and is reconstituted either with sterile distilled water or sterile isotonic saline. In general, nitrara-C is administered according to protocols in use with ara-C although at somewhat higher dosage levels.

I claim:

1. 1-(2-O-nitro-$\beta$-D-arabinofuranosyl)cytosine and its pharmaceutically-acceptable acid addition salts.

2. A compound according to claim 1, said compound being 1-(2-O-nitro-$\beta$-D-arabinofuranosyl)cytosine.

3. A salt of the compound of claim 2, said salt being 1-(2-O-nitro-$\beta$-D-arabinofuranosyl)cytosine hydrochloride.

4. A method for treating leukemia which comprises administering to a subject suffering from leukemia and who is in need of treatment an antileukemic amount of a compound according to claim 1.

5. A pharmaceutical formulation in unit dosage form adapted to achieve an anti-leukemia effect comprising, per dosage unit, an anti-leukemia amount of a compound according to claim 1 plus one or more pharmaceutical excipients.

* * * * *